(12) United States Patent
Chan et al.

(10) Patent No.: US 7,754,423 B2
(45) Date of Patent: Jul. 13, 2010

(54) METHODS FOR PREDICTING THE RISK OF DIABETIC NEPHROPATHY USING GENETIC MARKERS AND ARRAYS CONTAINING THE SAME

(75) Inventors: Juliana C. N. Chan, Hong Kong (CN); Maggie C. Y. Ng, Hong Kong (CN); Wing Yee So, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 688 days.

(21) Appl. No.: 10/591,824

(22) PCT Filed: Apr. 15, 2005

(86) PCT No.: PCT/CN2005/000508
§ 371 (c)(1), (2), (4) Date: Sep. 6, 2006

(87) PCT Pub. No.: WO2005/099335
PCT Pub. Date: Oct. 27, 2005

(65) Prior Publication Data
US 2007/0134673 A1    Jun. 14, 2007

(30) Foreign Application Priority Data
Apr. 15, 2004   (CN) ........................ 2004 1 0033864

(51) Int. Cl.
*C12Q 1/68* (2006.01)
*C12P 19/34* (2006.01)
(52) U.S. Cl. ......................................... 435/6; 435/91.2
(58) Field of Classification Search ........................ None
See application file for complete search history.

(56) References Cited

U.S. PATENT DOCUMENTS 6,197,505 B1 *  3/2001  Norberg et al. ................ 435/6

OTHER PUBLICATIONS

Nakamura et al. (2002) Clinical and Diagnostic Laboratory Immunology vol. 9 No. 4 pp. 935-937.*
Liu et al. (2002) Diabet. Med. vol. 19: pp. 113-118.*
Marre et al. (1997) J. Clin. Invest. vol. 99 No. 7: pp. 1585-1595.*
Neamat-Allah et al. (2001) Diabet. Med. vol. 18; pp. 906-914.*
Ko et al. (1995) Diabetes 44 (7), 727-732.*
Buck et al. (1999) BioTechniques 27: 528-536.*
Pei et al. *J. Clin. Invest.* 100(4):814-820 (1997).
Wang et al. *Diabetes Care.* 26(8):2410-2415 (2003).
Shu et al. *Kidney International.* 58:783-789 (2000).

* cited by examiner

*Primary Examiner*—Kenneth R. Horlick
*Assistant Examiner*—David C Thomas
(74) *Attorney, Agent, or Firm*—Knobbe Martens Olson & Bear LLP

(57) ABSTRACT

Disclosed is a method for detecting a Chinese diabetic subject suffering from, at risk for developing, or suspected of suffering from a nephropathy. The method includes determining whether a sample from the subject has at least one polymorphic sequence selected from the group consisting of polymorphic sequences an I/D genotype of an ACE gene, an M235T genotype of an AGT gene, a (CA) n-5' (z-2) genotype of an ALR2 gene, an C106T genotype of an ALR2 gene in the promoter region, a G-308A genotype of a TNF-α gene, and a complement thereof, provided that the ALR2 gene cannot be used alone, in which the presence of the polymorphic sequence indicates the subject suffering from, or at risk for suffering from a nephropathy. Also provided is an array for detecting a Chinese diabetic subject suffering from, or at risk for suffering from a nephropathy.

9 Claims, 3 Drawing Sheets

METHODS FOR PREDICTING THE RISK OF DIABETIC NEPHROPATHY USING GENETIC MARKERS AND ARRAYS CONTAINING THE SAME

RELATED APPLICATIONS

This application is the U.S. National Phase filing under 35 U.S.C. §371 of PCT/CN2005/000508, filed Apr. 15, 2005, which designated the United States and was published in English, which claims priority under 35 U.S.C. §119(a)-(d) to Chinese Patent Application No. 200410033864.X, filed Apr. 15, 2004. The content of these applications is incorporated herein by reference in their entireties.

FIELD OF THE INVENTION

The present invention relates to a method and an array for detecting a subject of Chinese descent suffering from, at risk for developing, or suspected of suffering from a nephropathy, by using one or more as markers, and particularly to a method and an array for detecting a nephropathy using one or more genetic polymorphisms selected from genes ACE, AGT, ALR2, and TNF-α, provided that ALR2 gene cannot be used alone.

BACKGROUND OF THE INVENTION

Diabetic nephropathy is a leading cause of morbidity and mortality in diabetic patients. With the rising epidemic of diabetes in both developing and developed countries, diabetes is now the leading cause of end stage renal disease (ESRD), accounting for 40-50% of all new patients on renal replacement therapy (Ritz E, Rychlik I, Locatelli F, Halimi S, End-stage renal failure in type 2 diabetes: a medical catastrophe of worldwide dimensions, *Am J Kidney Dis*, 1999; 34:795-808). China is one of the 3 top countries with the most number of diabetic people estimated to increase to 40 million in 2025 with the predominant increase occurring in the middle aged population (Chan J. C. N, Ng M. C. Y, Critchley J. A. J. H, Lee S. C, Cockram C. S, Diabetes mellitus a special medical challenge from a Chinese perspective, Diabetes Research and Clinical Practice, 2001; 54:S19-27). This is mainly due to the rising prevalence of young onset diabetes and childhood obesity and metabolic syndrome (Chan J. C. N, Ng M. C. Y, Lessons learned from young onset diabetes in China, Current Diabetes Report, 2003; 3:101-107; Chan J. C. N, Cheung C. K, Cheung M. Y F, Swaminathan R, Critchley J. A. J. H, Cockram C. S, Abnormal albuminuria as a predictor of mortality and renal impairment in Chinese patients with NIDDM, Diabetes Care, 1995; 18:1013-1014; Chan J. C. N, Ko G. T. C, Leung D, Cheung R. C. K, Cheung M, So W. Y, et al, The long term effects of angiotensin converting enzyme inhibition and metabolic control on cardiovascular and renal outcomes in hypertensive Type 2 diabetic patients, Kidney International, 2000; 57:590-600). In the World Health Organization Multinational Study for Vascular Diseases in Diabetes (WHO-MSVDD), Asian, notably Chinese and Japanese patients, had higher incidence of ESRD than Caucasian type 2 diabetic patients (Morrish N. J, Wang S, Stevens L. K, Fuller J. H, Keen H, Mortality and causes of death in the WHO Multinational Survey of Vascular Diseases in Diabetes, *Diabetologia*, 2001; 44:S14-21).

In contrast to the Caucasian diabetic population in whom the majority of patients die from cardiovascular events, ESRD is an important cause of death in Chinese diabetic patients (Chan J. C. N, Cheung C. K, Cheung MYF, Swaminathan R, Critchley J. A. J. H, Cockram C. S, Abnormal albuminuria as a predictor of mortality and renal impairment in Chinese patients with NIDDM, Diabetes Care, 1995; 18:1013-1014).These findings have recently been confirmed by the WHO-MSVDD (Morrish N. J, Wang S, Stevens L. K, Fuller J. H, Keen H, Mortality and causes of death in the WHO Multinational Survey of Vascular Diseases in Diabetes, *Diabetologia*, 2001; 44:S14-21). In keeping with these findings, it is now recognized there are inter-ethnic differences in the allele frequency or haplotypes of disease-associated genes which may contribute to the racial differences in susceptibility to disease development (Ng M, Wang Y, So W, Cheng S, Visvikis S, Zee R, et al, Ethnic differences in the linkage disequilibrium and distribution of single nucleotide polymorphisms in 35 candidate genes for cardiovascular diseases, Genomics, 2003: in press; Young R P, Thomas G. N, Critchley J. A. J. H, Tomlisnon B, Woo K. S, Sanderson J. E, Interethnic differences in coronary heart diseaes mortality in 25 populations: associations with the angiotensin converting enzyme DD genotype frequency, Journal of Cardiovascular Risk, 1998; 5:303-7). Given the effect of duration of disease on development of complications, rising prevalence of young and middle aged diabetic population and the racial predilection to develop diabetic renal disease, there is a looming epidemic of renal failure and cardiovascular diseases in our increasingly young population with its socioeconomical implications (Chan J. C. N, Ng M. C. Y, Critchley J. A. J. H, Lee S. C, Cockram C. S, Diabetes mellitus—a special medical challenge from a Chinese perspective, Diabetes Research and Clinical Practice, 2001; 54:S19-27).

We have previously reported the high prevalence of nephropathy ranging from 30% to 50% and the predictive value of this urinary marker for mortality and deterioration of renal function in Chinese diabetic subjects (Chan J C N, Cheung C K, Cheung M Y F, Swaminathan R, Critchley J A J H, Cockram C S, Abnormal albuminuria as a predictor of mortality and renal impairment in Chinese patients with NIDDM, Diabetes Care, 1995; 18:1013-1014; So W Y. Chan N, Tong P C Y, Chow C C, Chan W B, Ng M C Y, Chan J C N, Effect of RAAS inhibition on survival and renal outcomes in 3737 Chinese Type 2 diabetic patients, Hypertension. 2004; 44: 294-9).

Apart from hypertension and dyslipidemia, we have reported the independent association between insulin resistance and diabetic nephropathy (Chan J. C. N, Tomlinson B, Nicholls M. G, Swaminathan R, Cheung C. K, Cockram C S, Albuminuria, insulin resistance and dyslipidaemia in Chinese patients with non-insulin-dependent diabetes (NIDDM), Diabetic Medicine, 1996; 13:150-55) as well as the intimate relationships between obesity, albuminuria and dysglycemia in Chinese subjects (Lee Z, Critchley J, Ko G. T, Anderson P, Thomas N, Young R, et al, Obesity and cardiovascular risk factors in Hong Kong Chinese, Obesity Reviews, 2002; 3:178-182). Family-based studies and segregation analysis (The Diabetes Control and Complications Trial Research Group, Clustering of long term complications in families with diabetes in the diabetes control and complication trial, *Diabetes*, 1997; 46:1829-1839) as well as genome scan (Imperatore G, Hanson R L, Pettitt D, Kobes S, Bennett P, Knowler W, Sib pair linkage analysis for susceptibility genes for microvascular complications among Pima Indians with type 2 diabetes. Pima Diabetes Gene Group, *Diabetes*, 1998; 47:821-30; inperatore G, Knowler W, Pettitt D, Kobes S, Bennett P, Hanson R, Segregation analysis of diabetic nephropathy in Pima Indians, *Diabetes*, 2000; 49:1049-56) have confirmed strong genetic components in the development of diabetic renal disease. The renin angiotensin system (RAS)

plays a pivotal role in the regulation of systemic and renal haemodynamics as well as cellular and tissue growth (Cooper M, Pathogenesis, prevention and treatment of diabetic nephropathy, Lancet, 1998; 352:213-9). The TT genotype of the AGT M235T polymorphism and the D allele of the ACE I/D polymorphism have been associated with diabetic nephropathy in Caucasian, Japanese and Chinese diabetic patients (Fujisawa T, Ikegami H, Kawaguchhi Y, Hamada Y, Ueda H, Shintani M, et al, Meta analysis of association of insertion/deletion polymorphism of angiotensin I converting enzyme gene with diabetic nephropathy and retinopathy, Diabetologia, 1998; 41:47-53; Young R. P, Chan J. C. N, Poon E, Critchley J. A. J. H, Cockram C. S, Associations between albuminuria and angiotensinogen T235 and angiotensin converting enzyme insertion/deletion polymorphims in Chinese NIDDM patients, Diabetes Care, 1997; 21:431-7; Ringel J, Beige J, Kunz R, Distler A, Sharma A, Genetic variants of the renin angiotensin system, diabetic nephropathy and hypertension, Diabetologia, 1997; 40:193-9,. Wang Y, Ng M, So W, Tong P, Ma R, Chow C, Cockram C, JCN Chan. Prognostic effect of insertion/deletion polymorphism of the ace gene on renal and cardiovascular clinical outcomes in Chinese patients with type 2 diabetes. Diabetes Care, 2004; 28: 348-54).

Tumor necrosis factor alpha (TNF-α), a cytokine secreted by adipocytes, is the linking factor for obesity-related insulin resistance (Hotamisligil G S, Spiegelman B M, Tumor necrosis factor: a key component of the obesity-diabetes link, Diabetes, 1994; 43:1271-8), the latter being an important feature of diabetic nephropathy, including Chinese patients (Chan J. C. N, Tomlinson B, Nicholls M. G, Swaminathan R, Cheung C. K, Cockram C. S, Albuminuria, insulin resistance and dyslipidaemia in Chinese patients with non-insulin-dependent diabetes (NIDDM), Diabetic Medicine, 1996; 13:150-55). A recent Japanese study has shown a positive association between elevated serum TNF-α level and nephropathy in Type 2 diabetic patients (Moriwaki Y, Yamamoto T, Shibutani Y, Aoki E, Tsutsumi Z, Takahashi S, et al, Elevated levels of interleukin 18 and tumor necrosis factor alpha in serum of patients with type 2 diabetes mellitus: relationship with diabetic nephropathy, Metabolism: Clinical and Experimental, 2003; 52:605-8). In this regard, the G-308A polymorphism in the promoter region of TNF-α gene had been reported to be associated with obesity and insulin resistance (Dalziel B, Goskby A, Richman R, Bryson J, Caterson I, Association of TNF alpha-308 G/A promoter polymorphism with insulin resistance in obesity, Obesity Research, 2002; 10:401-7) and increased transcriptional activity of TNF-α (Kroeger K, Carville K, Abraham L, The 308 tumor necrosis factor alpha promoter polymorphism effects transcription, Molecular Immunolgy, 1997; 34:391-99). Aldose reductase (ALR2) is the key enzyme in the polyol pathway which can lead to increased oxidative stress and alteration of intracellular milieu causing diabetic microangiopathy (Hodgkinson A, Sondergaard K, Yang B, Cross D, Millward B, Demaine A, Aldose reductase expression is induced by hyperglycemia in diabetic nephropathy, Kidney International, 2001; 60:211-8). Both the z-2 allele of 5'-(CA) and T allele of C-106T polymorphisms of this gene have been shown to increase risk for nephropathy in Type 1 and Type 2 diabetic patients including Chinese (Wang Y, Ng M, Lee S, So W, Tong C, Cockram C, et al, Phenotypic heterogeneity associations of two aldose reductase gene polymorphisms with nephropathy and retinopathy in Type 2 diabetes, Diabetes Care, 2003; 26:2410-5). These putative genetic factors further interact with metabolic, hemodynamic and growth factors to cause proteinuria and progressive decline in renal function (Parving H. H, Tarnow L, Rossing P, Genetics of diabetic nephropathy, *Journal of American Society of Nephrology*, 1996; 7:2509-17).

Although there have been reports on the associations between these 5 genetic markers and diabetic complications in Caucasian and Japanese populations, there have been scanty and inconsistent reports in Chinese diabetic populations. To date, there have been no reports showing the interactive effects of these genetic factors on development of diabetic complications including diabetic nephropathy.

One of the promises of applied genomics lies in its potential use to identify at risk subjects for early and targeted intervention to preserve health and reduce the impact of killing diseases such as diabetes (Collins F, Green E, Guttmacher A, Guyer MobotuNHGRI, A vision for the future of genomics research. A blueprint for the genomic era, Nature, 2003; 422:835-47). In our search for genetic factors to identify high risk subjects for complications in Chinese diabetic patients, we were the first group to report the association between the AGT TT genotype and diabetic nephropathy and its synergistic effects with ACE D allele on its development (Young R P, Chan J. C. N, Poon E, Critchley J. A. J. H, Cockram C. S, Associations between albuminuria and angiotensinogen T235 and angiotensin converting enzyme insertion/deletion polymorphims in Chinese NIDDM patients, Diabetes Care, 1997; 21:431-7) as well as the independent predictive role of ACE DD genotype on development of ESRD (Wang Y, Ng M, So W, Tong P, Ma R, Chow C, Cockram C, JCN Chan. Prognostic effect of insertion/deletion polymorphism of the ace gene on renal and cardiovascular clinical outcomes in Chinese patients with type 2 diabetes. Diabetes Care. 2004; 28:348-54). Similarly, we were also the first group to report the risk association between ALR2 TT genotype (Wang Y, Ng M, Lee S, So W, Tong C, Cockram C, et al, Phenotypic heterogeneity associations of two aldose reductase gene polymorphisms with nephropathy and retinopathy in Type 2 diabetes, Diabetes Care, 2003; 26:2410-5). and diabetic nephropathy in subjects of Chinese descent.

SUMMARY OF THE INVENTION

Accordingly, the present invention relates to a method for detecting a Chinese diabetic subject suffering from, at risk for developing, or suspected of suffering from a nephropathy, the method comprising the step of:

determining whether a sample from the subject has at least one polymorphic sequence selected from the group consisting of polymorphic sequences an I/D genotype of an ACE gene, an M235T genotype of an AGT gene, a (CA)n-5'(z-2) genotype of an ALR2 gene, a C106T genotype of an ALR2 gene in the promoter region, a G-308A genotype of a TNF-α gene, and a complement thereof, provided that the ALR2 gene cannot be used alone, wherein the presence of the polymorphic sequence indicates the subject suffering from, or at risk for suffering from the nephropathy.

In an embodiment of the invention, the method may further comprise the step of providing a sample from the subject. The subject is preferably suffering from Type 2 diabetes. The sample is preferably blood.

The present invention also pertains to an array for detecting a subject of Chinese descent suffering from, at risk for developing, or suspected of suffering from a nephropathy, comprising at least one polymorphic sequence selected from the group consisting of sequences: an I/D genotype of an ACE gene, an M235T genotype of an AGT gene, a (CA)n-5'(z-2) genotype of an ALR2 gene, an C106T genotype of an ALR2 gene in the promoter region, a G-308A genotype of a TNF-α gene, and a complement thereof.

In the invention, the I/D polymorphism preferably comprises a DD genotype, and the G-308A polymorphism preferably comprises a GG genotype The present invention still relates to a kit for detecting a subject of Chinese descent suffering from, at risk for developing, or suspected of suffering from a nephropathy. The kit generally comprises an array define herein, and an instructional material teaching the processing of the sample with the array. Preferably, the kit may comprise a device for obtaining a sample from a subject.

DETAIL DESCRIPTION OF THE INVENTION

Figure 1:
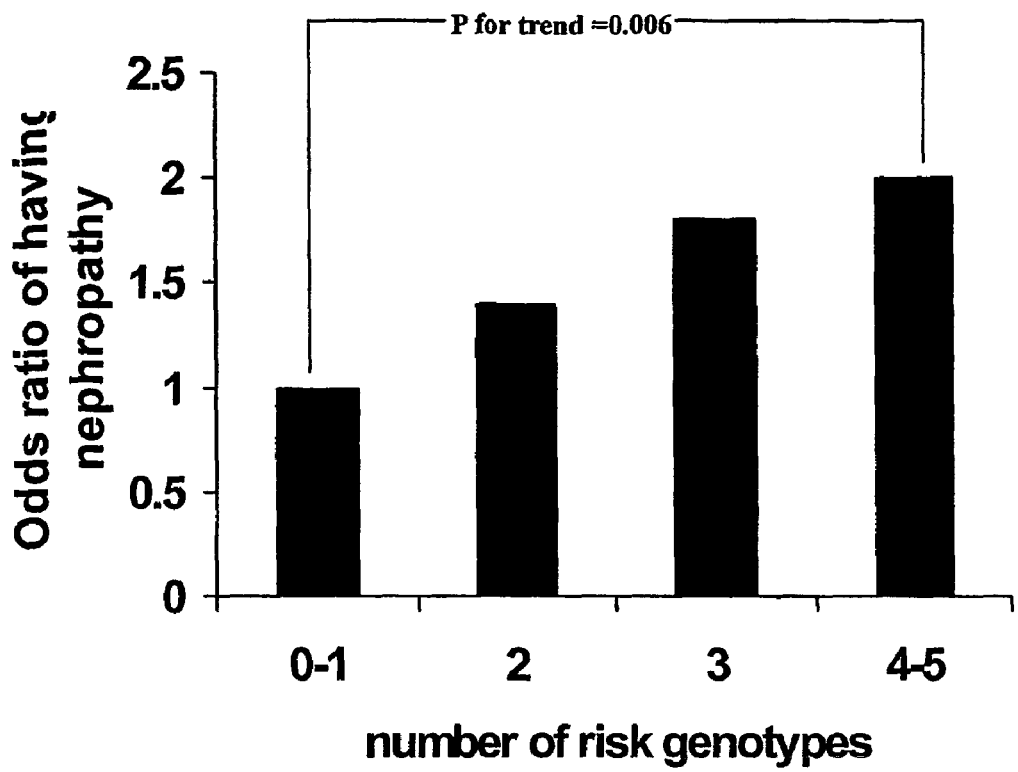
FIG. 1 shows the odds ratio of having nephropathy in the 711 Chinese Type 2 diabetic patients with different number of risk genotypes including a TT genotype of an AGT gene, a DD/DI genotype of an ACE gene, a GG genotype of an TNF-α gene, an x/z-2 or z-2/z-2 genotype and a CT/TT genotype of an ALR2 gene.

Genetic, epidemiological and experimental studies support the notion that multiple biochemical pathways are involved in diabetic nephropathy (Cooper M, Pathogenesis, prevention and treatment of diabetic nephropathy, Lancet, 1998; 352:213-9). Based on international and local as well as clinical and experimental evidence, we considered the TT genotype of AGT gene M235T, DD/ID genotype of ACE gene I/D, GG genotype of TNF-α gene G-308A, x/z-2 or z-2/z-2 genotype (x=any allele rather than z-2) and CT/TT genotype of ALR2 gene as potential risk genotypes for diabetic nephropathy in Chinese subjects.

Definitions

Unless specified otherwise in the invention, the term "AGT gene M235T" or "AGT M235T" is meant to "a M235T genotype of an AGT gene"; the term of "ACE gene I/D" or "ACE I/D polymorphism" has the same meaning of "an I/D genotype of an ACE gene"; the term of "GG of TNF-α gene" is equivalent to "GG genotype of TNF-α gene G-308A"; the term of "TNF-α gene G-308A" or "G-308A polymorphism in the promoter region of TNF-α gene" or "TNF-α G-308A" or "TNF α G308A polymorphism" is meant to "a G-308A genotype of a TNF-α gene"; the term of "z-2 allele of 5'-(CA)n of Aldose reductase (ALR2)" or "ALR2 (CA)n-5'(z-2)" is equivalent to "a (z-2) genotype of an ALR2 gene 5'-(CA) repeats"; the term "T allele of C-106T polymorphisms of Aldose reductase (ALR2)" is equivalent to "ALR2 TT genotype, TT of ALR2 gene" or "CT/TT genotype of ALR2 gene"; and the term of "a C-106T polymorphism of ALR2" is meant to "a C106T genotype of an ALR2 gene in the promoter region".

In the method in accordance with present invention for detecting a Chinese diabetic subject suffering from, at risk for developing, or suspected of suffering from a nephropathy, which comprises the step of determining whether the sample has at least one polymorphic sequence selected from the group consisting of polymorphic sequences an I/D genotype of an ACE gene, an M235T genotype of an AGT gene, a (CA)n-5'(z-2) genotype of an ALR2 gene, an C106T genotype of an ALR2 gene in the promoter region, a G-308A genotype of a TNF-α gene, and a complement thereof, provided that the ALR2 gene cannot be used alone, wherein the presence of the polymorphic sequence indicates the subject suffering from, at risk for, or suspected of suffering from kidney diseases.

Polymorphisms as genetic markers used in the method can be identified as follows:
(a) extracting a genomic DNA from a subject;
(b) amplifying by a PCR the genomic DNAs of ACE gene, AGT, TNF-α G-308A polymorphism, aldose reductase (ALR2) CA repeat, and promoter C106T of the ALR2 gene with the template of the human genomic DNA; and
(c) identifying the product of step (b) by gel-separation or sequencing.

In the present invention, the genomic DNA may be extracted from a fluid of the subject such as blood and urine. Blood is preferable.

Although the method for detection of the invention can be used for a subject, it is preferred for a subject who is suffering from Type 2 diabetes. The subject of Chinese descent is particularly suitable for the invention.

The four candidate genes selected in this study can all contribute to the development of diabetic nephropathy through plausible metabolic pathways. The AGT and ACE are important components of the RAS which contribute to hypertension and abnormal tissue growth (Cooper M, Pathogenesis, prevention and treatment of diabetic nephropathy, Lancet, 1998; 352:213-9; Ringel J, Beige J, Kunz R, Distler A, Sharma A, Genetic variants of the renin angiotensin system, diabetic nephropathy and hypertension, Diabetologia, 1997; 40:193-9). The cytokine TNF-α represents a link between obesity and insulin resistance (Hotamisligil G S, Spiegelman B M, Tumor necrosis factor: a key component of the obesity-diabetes link, Diabetes, 1994; 43:1271-8) and its serum level has been reported to be positively correlated with diabetic nephropathy (Moriwaki Y, Yamamoto T, Shibutani Y, Aoki E, Tsutsumi Z, Takahashi S, et al, Elevated levels of interleukin 18 and tumor necrosis factor alpha in serum of patients with type 2 diabetes mellitus: relationship with diabetic nephropathy, Metabolism: Clinical and Experimental, 2003; 52:605-8). The ALR2 contributes to development of diabetic microangiopathy through intracellular accumulation of sorbitol and increased oxidative stress under hyperglycemic conditions (Chung S, Ho E, Lam K, Chung S, Contribution of polyol pathway to diabetes-induced oxidative stress, Journal of American Society of Nephrology, 2003; 14:S233-6).

Figure 3A:
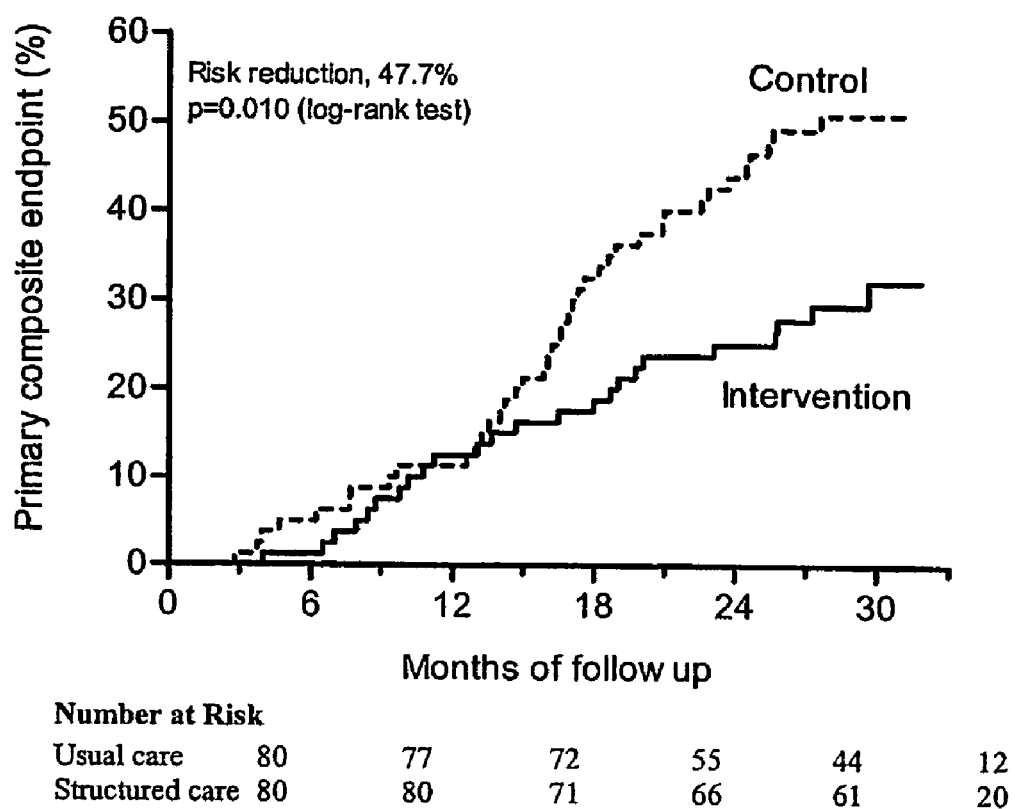
FIG. 3 shows Kaplan-Meier curves for the primary composite endpoint of end-stage renal disease or all-cause death (Panel A), end-stage renal disease (Panel B), and all-cause death (Panel C) in patients managed by a multidisciplinary team according to a protocol with particular emphasis on periodic monitoring, patient compliance and treatment to target (intervention group) versus usual clinic-based care (control group) where adherence to treatment guideline by doctors and patient compliance remained uncertain.
Figure 3B:
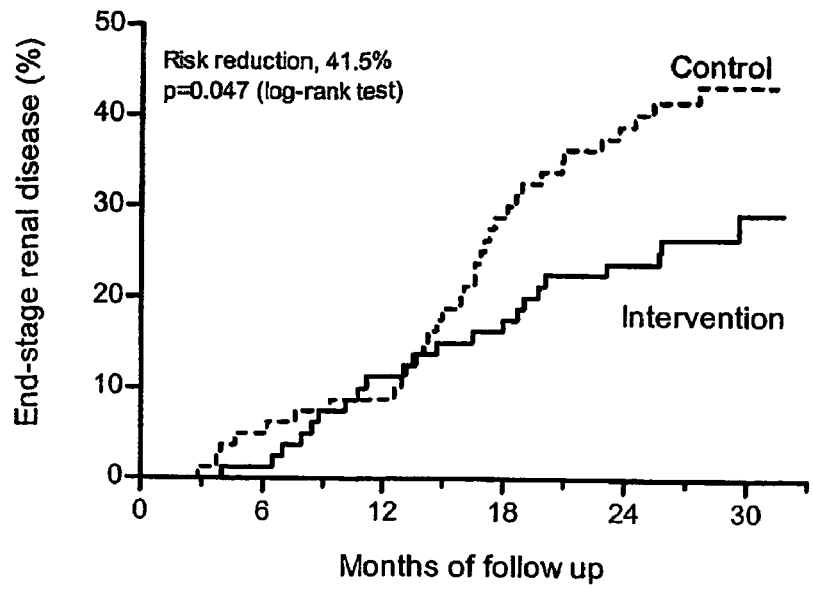
Figure 3C:
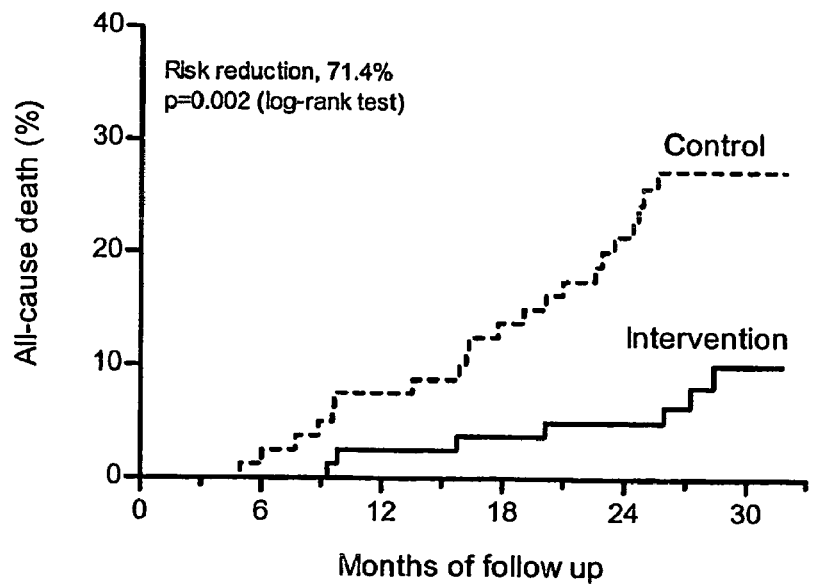

These genotypic findings in Chinese populations are based on a series of cross-sectional, prospective and case-control studies and are in consistence with the phenotypic features of patients with diabetic nephropathy who were more obese, hypertensive and had more adverse lipid and glycemic control than patients without nephropathy. Large scale randomized clinical studies have also confirmed the beneficial effects of inhibition of the RAS as well as improved glycemic and blood pressure control on diabetic proteinuria and development of ESRD (Brenner B. M, Cooper M. E, De Zeeuw D, Keane W. F. Mitch W. E, Parving H. H, et al, Effects of Losartan on renal and cardiovascular outcomes in patients with type 2 diabetes and nephropathy, New England Journal of Medicine, 2001; 345:861-9; UKPDS, Intensive blood glucose control with sulphonylureas or insulin compared with conventional treatment and risk of complications in patients with type 2 diabetes (UKPDS 33), Lancet, 1998; 352:837-53; Adler A. I, Stratton I. M, Neil H. A, Yudkin J. S, Matthews D. R, Cull C. A, et al, Association of systolic blood pressure with macrovascular and microvascular complications of type 2 diabetes (UKPDS 36): prospective observational study, British Medical Journal, 2000; 321:412-9). More recently, combination therapy with ACE and ALR2 inhibitors have been shown to act synergistically to improve nerve function in diabetic rats (Cotter M, Mirrlees D, Cameron N, Neurovascular interactions between aldose reductase and angiotensin converting enzyme inhibition in diabetic rats, European Journal of Pharmacology, 2001; 417:223-30). Taken together, identification of these genetic factors and their interactions (and the associated microchip technology to increase the efficiency of simultaneous screening for these risk genotypes in the same subject) should allow selection of high risk individuals for intensified and targeted therapy to reduce risk of complications. In this regard, we have demonstrated that a multifaceted approach using a multidisciplinary team with particular focus on periodic monitoring, treatment to target and reinforcement of patient compliance was associated with 40-70% risk reduction in development of death and ESRD in Chinese diabetic patients (FIG. 3). In light of the further increase in risk profile of subjects carrying these genotype(s), the benefits of this disease management protocol and its cost-effectiveness should be further enhanced.

After adjustment for age and sex, we found that the risk for having nephropathy increased progressively and significantly with increasing number of risk genotypes. Patients with 3 or more risk genotypes who accounted for 66% of our subjects, had 1.8-2.0 fold increased risk for diabetic nephropathy, compared to those patients with 0 or 1 risk genotype.

We have produced original data to confirm the predictive roles of DD genotype on development of ESRD, that of TNF-α on diabetic nephropathy especially in obese diabetic patients and more importantly, the interactions between these 5 genotypes on development of diabetic nephropathy.

It is understood that one or more genotypes mentioned above can be used to develop arrays that are used in conjunction with other known clinical, biochemical and genetic for predicting the risk of diabetic complications including nephropathy in Chinese diabetic patients, and these genotypes or equivalent arrays thereof can be used to identify at risk subjects for diabetes and/or diabetic renal disease for risk modification using a multifaceted approach including intensive monitoring, pharmacological and non-pharmacological therapy.

To practice the invention, it is convenient to use an array defined herein as a kit for detecting a Chinese diabetic subject suffering from, at risk for developing, or suspected of suffering from kidney diseases. The kit includes the array and a pair of primers for amplifying the genes ACE, AGT, ALR2 or TNF-α. In an embodiment of the kit of the invention, the primers are selected from SEQ ID NO: 1 to SEQ ID NO: 10.

The present invention also provides a kit which includes an array comprising at least one polymorphic sequence selected from the group consisting of: an I/D genotype of an ACE gene, an M235T genotype of an AGT gene, a (CA)n-5'(z-2) genotype of an ALR2 gene, an C106T genotype of an ALR2 gene in the promoter region, a G-308A genotype of a TNF-α gene, and a complement thereof, and optionally probes designed by the sequences as controls.

The present invention will be further described with the following Examples.

EXAMPLE 1

Identification of the Genotype of Five Polymorphic Sequences

Preparation of Human Genomic DNA

About 10 ml of EDTA blood was collected from each subject. The genomic DNA was extracted by lysing the cells with SDS and proteinase K overnight followed by extracting with phenol and chloroform. The DNA pellet was then dissolved in 1×TE buffer. The quantity and quality of the extracted DNA were determined by taking the optical densities at 260 nm and 280 nm. The extracted DNA was stored at 4° C. for next genotyping assays.

PCR Conditions for ACE Genes

Reactions were performed according to Rigat's Method (Rigat B, Hubert C, Alhenc-Gelas F, Cambien F, Corvol P, Soubrier F, An insertion deletion polymorphism in angiotensin I converting enzyme gene accounting for half the variance of serum enzyme levels, Journal of Clinical Investigation, 1990; 86:1343-1346) with modifications. 150 ng DNA templates were amplified using GeneAmp PCR System 9700 (ABI) in standard PCR buffer (50 nmM KCl, 10 mM Tris-HCl, pH 8.3, 3mM MgCl$_2$, 0.2 mM each dNTP)(ABI) with a primer concentration of 5 pmol each and 0.6U Tag Polymerase (Amersham). Total volume was 20 µl. The cycling conditions were as follows: initial denaturation at 94° C. for 2 min., 94° C. for 1 min., 58° C. for 1 min., 72° C. for 2 min. for a total of 30 cycles, and final extension 72° C. for 5 min. The sequence of the primer was:

SEQ ID NO. 1
5'CTG GAG ACC ACT CCC ATC CTT TCT 3'

SEQ ID NO.2
5'GAT GTG GCC ATC ACA TTC GTC AGA T 3'

The PCR product was a 190 bp fragment for the deletion and a 490 bp fragment for the presence of insertion allele.

PCR Conditions for Angiotensinogen Genes

Reactions were performed according to Russ's Method (Russ A, Maerz W. Ruzicka V, Stein U, Gross W, Rapid detection of the hypertension associated Met235→Thr allele of the human angiotensinogen gene, Human Molecular Genetics, 1994; 2:609-10). The PCR was performed in standard buffer (50 mM KCl, 10 mM Tris-HCl, pH 8.3, 1.5 mM MgCl$_2$, 50 uM each dNTP) (ABI) with a primer concentration of 0.3 uM each and 0.75 U Tag Polymerase(Amersham) with 200 ng DNA template in GeneAmp PCR system 9700 (ABI). Total volume was 20 µl. The sequence of the primer used in the reaction was:

SEQ ID NO.3
5'-CAG GGT GCT GTC CAC ACT GGA CCC C-3'

SEQ ID NO.4
5'-CCG TTT GTG CAG GGC CTG GCT CTC T-3'

Cycling conditions were as follows: denaturation at 90° C. 3 min., 10 cycles of 94° C. 1 min., 68° C. 1 min., 72° C. 1 min., followed by 30 cycles 90° C. 30 sec., 68° C. 1 min., and 72° C. 30 sec., a final extension 72° C. 10 min.

The PCR products were digested with 5 U Tth 111 I (Promega) at 65° C. overnight. The digested fragments were separated by electrophoresis in 3% agarose gel. The homozygous methionine allele appeared as a non-digested single 165 bp and threonin allele as digested 141 and 24 bands.

PCR Conditions for TNF-α G-308A Polymorphism

Reactions were performed as described by Wilson et al (Wilson A, di Giovine F, Blakemore A, Duff G, Single base polymorphism in the human tumor necrosis factor alpha gene detectable by NcoI restriction of PCR product, Human Molecular Genetics, 1992; 1:535). The reaction was performed with GeneAmp PCR system 9700 (ABI) in a final volume of 20 μl containing 100 ng DNA template, 50 mM KCl, 10 mM Tris-HCl, pH 8.3, 2.5mM $MgCl_2$, 0.2 mM each dNTP(Boehringer-Mannheim, Germany) using a primer concentration of 0.5 mM each and 0.05 U Taq polymerase (Boehringer-Mannheim, Germany). The sequence of the primer used in the reaction was as follows:

```
                                          SEQ ID NO.5
    5'-AGG CAA TAG GTT TTG AGG GCC AT-3'

SEQ ID NO.6
    5'-TCC TCC CTG CTG CTC CGA TTC CG-3'
```

Cycling conditions were as follows: initial denaturation at 95° C. for 3min., 35 cycles of 95° C. 1 min., 58° C. 1 min., and 72° C. 1 min., final extension 72° C. 10 min. The amplified PCR products were digested with 10 U NcoI (Promega) at 37° C. overnight. The digested fragments were separated by electrophoresis in 3% agarose gel. The A allele gave a band size of 107 bp while the G allele produced 87 bp and 20 bp fragments.

PCR Conditions for Aldose Reductase (ALR2) CA Repeats

The region containing CA dinucleotide repeat was amplified by PCR with primers that flanked a 138 bp region using the method described by Ko et al (Ko B. C. B, Lam K. S. L, Wat N. M. S, Chung S. S. M, An (A-C)n dinucleotide repeat polymorphic marker at the 5' end of the aldose reductase gene is associated with early onset diabetic retinopathy in NIDDM patients, Diabetes, 1995; 44:727-32). The forward primer used in the reaction was as follows:

```
                                          SEQ ID NO.7
    5'-GAA TCT TAA CAT GCT CTG AAC C-3'
``` and the reverse primer was:

```
                                          SEQ ID NO.8
    Arpr2 5'-GCC CAG CCC TAT ACC TAG T-3'.
```

An M13 tail (5'-CAC GAC GTT GTA AAA CGA C-3') was added to 5' end of the forward primer for labelling of infrared fluorescence.

A PCR was carried out in a total volume of 4 μl with 1 ng genomic DNA, 2.5 mM $MgCl_2$, 0.2 mM of each dNTP, 0.1 pmol/μl of each primer, 0.15 pmol/μl 1 of IRD800 labelled M13 forward (-29) primer, and 0.15 U Taq polymerase (Amplitaq, Perkin-Elmer/Cetus, Norwalk, Conn.) in the buffer prepared according to the supplied recipe. Cycling conditions were as follows: initial denaturation at 94° C. for 3 min., 35 cycles 94° C. 1 min., 57° C. 1 min., 72° C. 1 min., and a final extension 72° C. 10 min.

The amplified PCR products were heated at 95° C. for 5 mins and then loaded onto 5.5% denaturing polyacrylamide gel and resolved electrophoretically in 0.8×TBE at constant power 75 W and 55° C. using Li-COR DNA Analyser (Li-COR, Lincoln, Nebr.). Alleles were sized by comparing a plasmid DNA containing a 23(CA) repeats of ALR2 gene which was kindly provided by Dr. Shiro Maeda from Shiga University of Medical Science of Japan.

PCR Conditions for Promoter C106T of ALR2 Genes

Reactions were performed as described by Kao Y L et al (Kao Y, Donaghue K, Chan A, Knight J, Silink M, A novel polymorphism in the aldose reductase gene promoter region is strongly associated with diabetic retinopathy in adolescents with type 1 diabetes, Diabetes, 1999; 48:1338-40). The reaction was performed with GeneAmp PCR system 9700 (ABI) in a final volume of 20 ul containing 100 ng DNA template, 50 mM KCl, 10 mM Tris-HCl, pH 8.3, 2mM $MgCl_2$, 0.2 mM each dNTP(Boehringer-Mannheim, Germany) using a primer concentration of 0.5 pmol/μl each and 0.5 U Taq polymerase (Boehringer-Mannheim, Germany). The sequence of the primer used was as follows:

```
                                          SEQ ID NO.9
    5'-CCT TTC TGC CAC GCG GGG CGC GGG-3'

SEQ ID NO.10
    5'-CAT GGC TGC TGC GCT CCC CAG-3'
```

Cycling conditions were as follows: initial denaturation at 94° C. for 3min., 35 cycles of 94° C. 1 min., 57° C. 1 min., and 72° C. 1 min., a final extension 72° C. 10 min. The amplified PCR products were digested with 5 U BfaI (New England Biolabs, Beverly, Mass.) at 37° C. overnight. The digested fragments were separated by electrophoresis in 3.5% agarose gel. The C allele was indicated by 206 bp and 57 bp fragments while the 206 bp fragment was further cleaved into 147 bp and 59 bp for the T allele.

EXAMPLE 2

Relationship of Gene-Gene Interactions with Nephropathy

We examined the interactive effects of AGT gene M235T, ACE (I/D), TNF-α gene G-308A, ALR gene 5'-$(CA)_n$ and promoter C-106T polymorphisms in 711 Chinese Type 2 diabetic patients (303 male and 408 female, aged 63.1±11.1 years). Patients who had duration of diabetes >10 years and plasma creatinine <100 μmol/l and spot urine albumin creatinine ratio (ACR) <3.5 mg/mmol were selected as control cases (n=388). Patients who had either plasma creatinine ≧150 μmol/l or ACR ≧25 mg/mmol were considered to have nephropathy (n=323). Statistical Package for Social Science (Version 10.0, SPSS Inc, Chicago) was used for statistical analysis with logarithmic transformation of skewed data including triglyceride and ACR. Continuous variables were expressed as means±SD or geometric means×/÷antilog SD where appropriate. Between groups comparisons were analyzed using Independent Sample T-Test and Analysis of Covariance. The Chi-square test was used to analyze allele and genotype frequencies and percentage of various diabetes-related metabolic abnormalities and complications. The odds ratio (OR) with 95% confidence intervals (CI) was calculated for the risk of diabetic nephropathy among patients with different number of risk genotypes. A P value of <0.05(2-tailed) was considered to be significant. Patients with nephropathy were older with a male predominance compared to patients without nephropathy. After adjustment for age and sex, patients with nephropathy were more obese with higher body mass index (BMI) and waist-hip ratio (WHR) as well as higher blood pressure than patients without nephropathy. They also had more adverse lipid profile with higher serum total cholesterol (TC), triglyceride (TG) and lower HDL-C and were more likely to have sensory neuropathy, retinopathy, peripheral vascular disease and coronary heart disease. Table 1 showed comparisons of clinical and biochemical parameters between patients with and without nephropathy in the 711 Chinese Type 2 diabetes. Data were expressed as Mean±SD or a Geometric mean×/÷antilog SD, and were compared by Independent-Sample T test between patients without and with nephropathy. Percentage of diabetic complications was compared by Chi-square test between two study groups.

TABLE 1

| | Study Groups | | | |
|---|---|---|---|---|
| | No Nephropathy (N = 323) | Nephropathy (N = 388) | P Value | Adjusted P Value* |
| Sex (% of Male) | 30.0 | 53.1 | <0.001 | — |
| Age (years) | 60.6 ± 10.1 | 65.1 ± 11.6 | <0.001 | — |
| Duration of Diabetes (years) | 16.0 ± 1.6 | 8.2 ± 5.4 | <0.001 | — |
| Body mass Index (kg/m$^2$) | 23.9 ± 3.2 | 25.5 ± 4.0 | <0.001 | <0.001 |
| Waist Height Ratio | 0.87 ± 0.06 | 0.91 ± 0.07 | <0.001 | <0.001 |
| Systolic Blood Pressure (mmHg) | 131 ± 18 | 153 ± 23 | <0.001 | <0.001 |
| Diastolic Blood Pressure (mmHg) | 72 ± 10 | 83 ± 12 | <0.001 | <0.001 |
| HbA$_{1c}$ (%) | 7.6 ± 1.3 | 8.1 ± 2.1 | <0.001 | <0.001 |
| Fasting Plasma Glucose (mmol/l) | 8.3 ± 2.8 | 9.5 ± 4.4 | <0.001 | <0.001 |
| Total Cholesterol (mmol/l) | 5.2 ± 1.0 | 5.9 ± 1.5 | <0.001 | <0.001 |
| Triglyceride (mmol/l)$^a$ | 1.1 ×/÷ 1.7 | 1.9 ×/÷ 1.9 | <0.001 | <0.001 |
| HDL-C (mmol/l) | 1.4 ± 0.4 | 1.2 ± 0.3 | <0.001 | <0.001 |
| LDL-C (mmol/l) | 3.20 ± 0.84 | 3.73 ± 1.21 | <0.001 | <0.001 |
| Plasma Creatinine (μmol/l) | 72.4 ± 14.3 | 152.6 ± 105.4 | <0.001 | <0.001 |
| Albumin Creatinine Ratio (mg/mmol)$^a$ | 1.1 ×/÷ 2.0 | 128.8 ×/÷ 2.9 | <0.001 | <0.001 |
| Obesity (%) | 34.5 | 47.9 | <0.001 | <0.001 |
| Hypertension (%) | 46.7 | 81.2 | <0.001 | <0.001 |
| Dyslipidaemia (%) | 52.0 | 83.0 | <0.001 | <0.001 |
| Retinopathy (%) | 25.1 | 54.6 | <0.001 | <0.001 |
| Neuropathy (%) | 18.6 | 43.8 | <0.001 | <0.001 |
| Peripheral Vascular Disease (%) | 2.8 | 13.4 | <0.001 | <0.001 |
| Ischemic Heart Disease (%) | 5.9 | 12.4 | 0.003 | 0.019 |
| Cerebrovascular Disease (%) | 3.7 | 8.5 | 0.009 | 0.098 |
| Use of RAS Inhibitors (%) | 26.9 | 79.9 | <0.001 | — |

*P value after adjustment for age and sex using analysis of covariance.

Table 2 summarized the distribution of these 5 genotypes in patients with or without nephropathy. Genotype and allele frequencies were compared by Chi-square test between patients with and without neplhropathy. Patients with nephropathy had higher frequency of z-2 of the 5'-(CA)$_n$ (24.1% vs. 18.6%, P=0.O1) and T allele of the C-106T (25.8% vs. 21.4%, P=0.05) of ALR2 gene than patients without nephropathy. The z-2 allele carriers of ALR2 5'-(CA)$_n$ had higher ACR level (17.8×/÷12.3 vs. 12.6×/÷12.9 mg/mmol, P=0.062) and percentage of retinopathy (47.4% vs. 37.4%, P=0.009) than the non z-2 carriers. The DD/DI genotype carriers of ACE I/D had higher TC level than the II genotype carriers (5.7±1.4 vs 5.5±1.3 mmol/l, P=0.047). The obese GG genotype carriers of TNF-α gene G-308A had higher ACR (22.9×/÷11.5 vs 10.7×/÷13.2 mg/mmol, P<0.001) and plasma creatinine level (125±95 vs. 108±75 μmol/l, P=0.005) than non-obese subjects after adjustment for age and sex.

TABLE 2

| | Genotype Frequency (%) | | | Allele Frequency (%) | |
|---|---|---|---|---|---|
| Genotypes of Gene Polymorphisms | No Nephropathy (N = 323) | Nephropathy (N = 388) | Alleles of Gene Polymorphisms | No Nephropathy (N = 646) | Nephropathy (N = 776) |
| AGT gene M235T | | | AGT gene M235T | | |
| TT | 70.9 | 72.9 | T | 84.4 | 85.7 |
| TM | 26.9 | 25.5 | | | |
| MM | 2.2 | 1.5 | M | 15.6 | 14.3 |
| ACE Gene I/D | | | ACE Gene I/D | | |
| II | 45.8 | 46.4 | I | 66.6 | 67.3 |
| DI | 41.5 | 41.8 | | | |
| DD | 12.7 | 11.9 | D | 33.4 | 32.7 |
| TNF-α Gene G-308A | | | TNF-α Gene G-308A | | |
| GG | 80.8 | 84.0 | G | 89.9 | 91.8 |
| GA | 18.3 | 15.5 | | | |
| AA | 0.9 | 0.5 | A | 10.1 | 8.2 |
| ALR2 Gene | | | ALR2 Gene | | |

TABLE 2-continued

| Genotypes of Gene Polymorphisms | Genotype Frequency (%) | | Alleles of Gene Polymorphisms | Allele Frequency (%) | |
|---|---|---|---|---|---|
| | No Nephropathy (N = 323) | Nephropathy (N = 388) | | No Nephropathy (N = 646) | Nephropathy (N = 776) |
| 5'-(CA)$_n$ | | | 5'-(CA)$_n$ | | |
| x/x | 67.2 | 57.7 | x | 81.4 | 75.9 |
| x/z − 2 | 28.5 | 36.3 | | | |
| z − 2/z − 2 | 4.3 | 5.9* | z − 2 | 18.6 | 24.1+ |
| ALR2 Gene 5'-(CA)$_n$ | | | ALR2 Gene 5'-(CA)$_n$ | | |
| y/y | 89.9 | 93.3 | y | 94.4 | 96.6 |
| y/z + 6 | 9.3 | 6.7 | | | |
| z + 6/z + 6 | 0.9 | 0** | z + 6 | 5.6 | 3.4++ |
| ALR2 Gene C-106T | | | ALR2 Gene C-106T | | |
| CC | 63.5 | 56.7 | C | 78.6 | 74.2 |
| CT | 30.3 | 35.1 | | | |
| TT | 6.2 | 8.2*** | T | 21.4 | 25.8+++ | x = any other (CA)n alleles rather than z − 2 allele;
y = any other (CA)n alleles rather than z + 6 allele;
*P = 0.01, P = 0.09, *P = 0.07, when the combined genotype frequencies of ALR2 gene x/z − 2 or z − 2/z − 2, y/z + 6 or z + 6/z + 6 and CT/TT were compared between patients with and without nephropathy, respectively;
+P = 0.01, ++P = 0.04, +++P = 0.05, when the z − 2, z + 6 and T allele frequencies of ALR2 gene were compared between patients with and without nephropathy, respectively.

Table 3 summarizes the distribution of number of genotypes in this patient cohort. Of the 711 Chinese Type 2 diabetic patients, 64 (9.0%) had 0 or 1 risk genotype, 176 (24.8%) had 2 risk genotypes, 290 (40.8%) had 3 risk genotypes and 181 (25.5%) had 4 or 5 risk genotypes. Compared to patients with ≦1 risk genotype, the odds ratio of having nephropathy increased from 1.4 (95% CI 0.8-2.4, P=0.3) to 1.8 (95% CI 1.1-1.3, P=0.03) and to 2.0 (95% CI 1.1-3.6, P=0.02) in patients with 2, 3 and ≧4 risk genotypes, respectively (P=0.006 for trend) (FIG. 1).

TABLE 3

| Number of Risk Genotypes | No Nephropathy | Nephropathy | Whole Cohort N (%) |
|---|---|---|---|
| 0 Risk Genotype | 6 | 2 | 8 (1.1) |
| 1 Risk Genotype | 31 | 25 | 56 (7.9) |
| 2 Risk Genotypes | 88 | 88 | 176 (24.8) |
| 3 Risk Genotypes | 125 | 165 | 290 (40.8) |
| 4 Risk Genotypes | 58 | 87 | 145 (20.4) |
| 5 Risk Genotypes | 15 | 21 | 36 (5.1) |
| Total | 323 | 388 | 711 |

EXAMPLE 3

Relationship of TNF-α GG Genotypes with Nephropathy

Table 4 indicates the effects of interaction between obesity and G-308A polymorphism of TNF-α gene on the development of nephropathy in Chinese Type 2 diabetic patients, in which "Ref" represent a referent group using the non-obese GA/AA carriers. Obese subjects with GG genotype had 1.9-fold increased risk (95% CI: 1.1-3.2, P=0.012) for having nephropathy.

TABLE 4

| | Frequency No. (%) | | Risk of Nephropathy | | P Value |
|---|---|---|---|---|---|
| Groups | Nephropahty− | Nephropahy+ | OR | 95% CI | |
| GG−/Obesity− (Ref.) | 40 (12.4) | 38 (9.8) | 1 | | |
| GG−/Obesity+ | 22 (6.8) | 24 (6.2) | 1.2 | 0.55-2.38 | 0.710 |
| GG+/Obesity− | 172 (53.1) | 164 (42.3) | 1.0 | 0.62-1.65 | 0.970 |
| GG+/Obesity+ | 89 (27.6) | 162 (41.8) | 1.9 | 1.15-3.20 | 0.012 |

Table 5 shows the multiple logistic regression analysis to examine the role of interaction of TNF-α gene G-308A with obesity on nephropathy after adjustment for confounding factors including age, male gender, fasting plasma glucose, hypertension, dyslipidaemia, retinopathy, neuropathy and peripheral vascular disease, the risk for nephropathy increased by an additional 2.4 fold (95% CI 1.3-4.5, P=0.007) amongst obese patients with GG genotype in 711 Chinese Type 2 diabetic patients. In Table 5, overall percentage correct is 75.2%; dependent variable is: code=1 for nephropathy; independent variables include age, sex (code=1 for male), HbA$_{1c}$, FPG, presence of dyslipidaemia, hypertension, retinopathy, neuropathy, peripheral vascular disease, ischemic heart disease and cerebrovascular disease (code=1), and interaction between the TNF-α gene G-308A polymorphism and obesity is: GG−/Obesity− (code=0), GG−/Obesity+ (code=1), GG+/Obesity− (code=2), GG+/Obesity+ (code=3).

TABLE 5

| Independent Predictors | Risk for Having Nephropathy | | |
|---|---|---|---|
| | Odds Ratio | 95% CI | P Value |
| Age (year) | 1.02 | 1.002-1.04 | 0.033 |
| Male Gender | 2.6 | 1.78-3.71 | <0.001 |
| Fasting Plasma Glucose (mmol/l) | 1.1 | 1.03-1.16 | 0.002 |
| Dyslipidaemia | 2.8 | 1.86-4.18 | <0.001 |
| Hypertension | 3.2 | 2.19-4.81 | <0.001 |
| Retinopathy | 2.4 | 1.62-3.51 | <0.001 |
| Neuropathy | 2.1 | 1.36-3.22 | 0.001 |
| Peripheral Vascular Disease | 2.8 | 1.21-6.59 | 0.017 |
| GG−/Obesity+ vs GG−/Obesity− | 1.4 | 0.57-3.26 | 0.482 |
| GG+/Obesity− vs GG−/Obesity− | 1.2 | 0.64-2.15 | 0.614 |
| GG+/Obesity+ vs GG−/Obesity− | 2.4 | 1.27-4.48 | 0.007 |

EXAMPLE 4

Relationship of ACE II/DD Genotype with Nephropathy

In an expanded cohort of 947 Chinese Type 2 diabetic patients with a mean follow-up period of 4.0±1.4 years, we examined the impact of ACE II/DD genotype on development of ESRD defined as renal death or events (need for dialysis or plasma creatinine >500 μmol/l or doubling of plasma creatinine of baseline value >150 μmol/l). Of these 947 patients, 62 patients developed renal endpoint.

Table 6 shows the genotype and allele frequencies of ACE I/D polymorphism in 947 Chinese Type 2 diabetic patients with and without occurrence of renal endpoint defined as doubling of baseline plasma creatinine or need for dialysis after a median follow-up period of 4.0 years. Genotype and allele frequencies were compared by Chi-square test between patients with and without renal endpoints.

Figure 2:
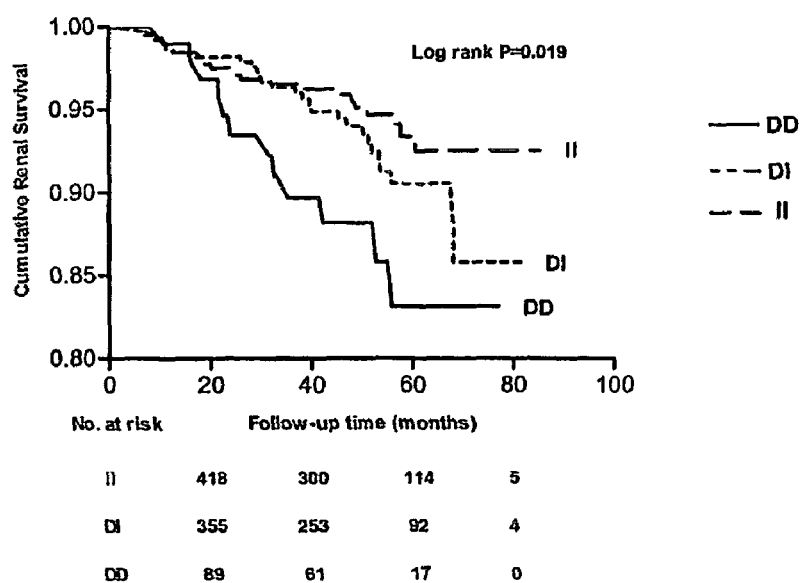
FIG. 2 shows Kaplan-Meier curves for renal endpoint among carriers of ACE gene I/D genotypes in 947 Chinese Type 2 diabetic patients.

From Table 6, the former group had higher DD genotype (19.4% vs. 9.8%, P=0.031) and D allele frequency (41.2% vs. 30.2%, P=0.011) than patients who did not develop renal endpoint. Kaplan-Meier analysis showed that there was significant difference in cumulative renal survival rate among patients with II (23 of 460 patients developed renal endpoint), DI (27 of 388 patients developed renal endpoint) and DD (12 of 99 patients developed renal endpoint) genotypes (log-rank P=0.019) (FIG. 2).

TABLE 6

| | Status of Occurring of Renal Endpoint | |
|---|---|---|
| | Non-Occurrence | Occurrence |
| Genotype Frequency (%) | | |
| II | 49.4 | 37.1 |
| DI | 40.8 | 43.5 |
| DD | 9.8 | 19.4† |
| Total No. of Genotype | 885 | 62 |
| Allele Frequency (%) | | |
| I | 69.8 | 58.8 |
| D | 30.2 | 41.2‡ |
| Total No. of Allele | 1771 | 124 |

†P = 0.031,
‡P value = 0.011 when the genotype and allele frequencies were compared between patients with and without occurrence of renal endpoint, respectively.

Table 7 shows the multiple Cox-regression analysis to examine the predictors for renal endpoint in 947 Chinese Type 2 diabetic patients, in which "a" represents patients who were present of micro- or macroalbuminuria at baseline; "b" represents DI genotype carriers compared to II genotype carriers; and "c" represents DD genotype carriers compared to II genotype carriers. Dependent variables include: Renal death and event (code=1), and independent variables include: age, sex (code=1 for male), duration of diabetes, SBP, DBP, TC, log value of TG, HDL-C, LDL-C, presence of complications (code=1) including nephropathy, retinopathy, neuropathy and peripheral vascular disease at baseline, as well as ACE gene I/D polymorphism (code=1 for DI vs. II, code=2 for DD vs. II).

In multiple Cox-regression analysis, the occurrence of renal endpoint remained significantly influenced by I/D polymorphism with a dominant deleterious effect of the DD genotype (DD vs. II, adjusted hazard ratio 3.4, 95% CI 1.6-7.3, P=0.002). Other independent predictors included long duration of diabetes, high systolic blood pressure, triglyceride, presence of nephropathy and retinopathy at baseline.

TABLE 7

| Independent Variables (at baseline) | β Coefficient | Hazard Ratio | 95% CI | P Value |
|---|---|---|---|---|
| Duration of Diabetes (years) | 0.050 | 1.05 | 1.01-1.09 | 0.013 |
| Systolic Blood Pressure (mmHg) | 0.014 | 1.01 | 1.00-1.03 | 0.012 |
| Log Value of Triglyceride (mmol/l) | 2.063 | 7.87 | 2.24-27.7 | 0.001 |
| Presence of Nephropathy[a] | 3.579 | 35.8 | 4.84-265.2 | 0.001 |
| Presence of Retinopathy | 0.850 | 2.34 | 1.27-4.30 | 0.006 |
| DI Genotype Carriers of ACE Gene I/D[b] | 0.595 | 1.81 | 0.99-3.31 | 0.053 |
| DD Genotype Carriers of ACE Gene I/D[c] | 1.223 | 3.40 | 1.59-7.27 | 0.002 |

EXAMPLE 5

Relationship of ALR2 Genotypes with Nephropathy

In a consecutive cohort of 738 Chinese Type 2 diabetic patients [age 55.5±13 years, known disease duration 5.7±5.7 years, means±SD], 21.5% had nephropathy (DN) only, 8% had retinopathy (DR) only, 16.4% had both nephropathy and retinopathy (DNDR) and 53.1% were free from complications (UC). The CT/TT genotype carriers (N=267) had a higher urinary AER than the CC genotype carriers (N=471) (30.2×/÷7.2 vs. 21.9×/÷6.9 μg/min, P=0.03). This difference remained significant (P=0.04) after adjustment for confounding variables including age, duration of diabetes, blood pressure and $HbA_{1c}$.

Since duration of disease is a major determinant for development of diabetic microvascular complications (Rogus J. J, Warram J. H, Krolewski A. S, Genetic studies of late diabetic complications. The overlooked importance of diabetes duration before complication onset, Diabetes, 2002; 51:1655-1662), patients with less than 5 years of diabetes (n=300) were excluded in a subsequent analysis. The remaining patients (n=438) were divided into four subgroups: 159 (36.3%) patients with DN only, 66 (15.1%) patients with DR only, 121 (27.6%) patients with both DNDR and 92 (21%) patients were uncomplicated (UC). Univariate analysis revealed higher frequencies of the z-2 allele (25.7% vs. 16.9%, OR 1.7, 95% CI 1.0-2.8, P=0.03) and the T allele (26.4% vs. 18.5%, OR 1.6, 95% CI 1.0-2.7, P=0.04) in the DNDR group compared with the UC group.

Using age, sex, duration of disease, BP, metabolic indices and the three ALR2 genotypes (z+6 carrying, z-2 carrying and CT/TT) as independent variables and the UC group as control (code=0), the z-2 carrying (OR 2.64, 95% CI 1.02-5.83) and CT/TT genotypes (OR 2.48, 95% CI 1.19-5.19) together with age (OR 1.06, 95% CI 1.02-1.10), BP (OR 1.04, 95% CI 1.02-1.06), $HbA_{1c}$ (OR 1.23, 95% CI 1.03-1.46), log TG (OR 20.1, 95% CI 3.73-107.7) and male gender (OR 2.25, 95% CI 1.10-4.61) were independent risk factors for prediction of DNDR with 76.9% correct rate.

What we claim is:

1. A method for detecting a diabetic subject at risk for developing a nephropathy, comprising the step of determining whether a sample from the subject has polymorphic sequences comprising an I/D genotype of an angiotensin converting enzyme (ACE) gene, a (z-2) genotype of an aldose reductase (ALR2) gene 5'-(CA) repeats, and a C106T genotype of an ALR2 gene in the promoter region, or a complement thereof,
wherein the presence of the polymorphic sequences indicates that the subject is at risk for developing the nephropathy.

2. The method of claim 1, wherein the sample is blood.

3. The method of claim 1, further comprising the step of amplifying the ACE and ALR2 genes.

4. The method of claim 3, wherein the amplifying step is performed with primers having SEQ ID NO. 1 and SEQ ID NO. 2 for the I/D genotype of the ACE gene, SEQ ID NO. 7 and SEQ ID NO. 8 for a (z-2) genotype of the ALR2 gene, and SEQ ID NO. 9 and SEQ ID NO. 10 for a C106T genotype of the ALR2 gene in the promoter region.

5. The method of claim 2, wherein the subject is at risk for developing Type 2 diabetes.

6. The method of claim 2, wherein the I/D genotype comprises a DD genotype.

7. The method of claim 1, wherein the polymorphic sequences further comprise an M235T genotype of an angiotensinogen (AGT) gene, or a G-308A genotype of a tumor necrosis factor alpha (TNF-α) gene.

8. The method of claim 7, wherein the G-308A genotype comprises a GG genotype.

9. The method of claim 7, wherein the primers used for amplifying further comprise SEQ ID NO. 3 and SEQ ID NO. 4 for an M235T genotype of the AGT gene; or SEQ ID NO. 5 and SEQ ID NO. 6 for a G-308A genotype of the TNF-α gene.

* * * * *

UNITED STATES PATENT AND TRADEMARK OFFICE
CERTIFICATE OF CORRECTION

| | |
|---|---|
| PATENT NO. | : 7,754,423 B2 |
| APPLICATION NO. | : 10/591824 |
| DATED | : July 13, 2010 |
| INVENTOR(S) | : Chan et al. |

It is certified that error appears in the above-identified patent and that said Letters Patent is hereby corrected as shown below:

Column 1, Line 41, Change "mellitus a" to --mellitus—a--.

Column 2, Line 18, Change "diseaes" to --diseases--.

Column 2, Line 38, Change "Y." to --Y,--.

Column 2, Line 63, Change "inperatore" to --Imperatore--.

Column 3, Line 15, Change "polymorphims" to --polymorphism--.

Column 3, Line 49, Change "308" to -- -308--.

Column 3, Line 51, Change "Immunolgy," to --Immunology,--.

Column 4, Line 24, Change "polymorphims" to --polymorphism--.

Column 4, Line 36, Change "2003; 26:2410-5))." to --2003; 26:2410-5)--.

Column 5, Line 3, Change "genotype" to --genotype.--.

Column 6, Line 66, Change "F." to --F,--.

Column 8, Line 27, Change "nmM" to --mM--.

Column 8, Line 47, Change "W." to --W,--.

Column 9, Line 59, Before "of IRD800" delete "1".

Column 10, Line 15, Change "ul" to --µl--.

Signed and Sealed this
Twenty-fifth Day of January, 2011

David J. Kappos
*Director of the United States Patent and Trademark Office*

Column 10, Line 44, Change "ALR" to --ALR2--.

Column 12, Line 28,(Approx.) Change "neplhropathy." to --nephropathy.--.

Column 12, Line 30,(Approx.) Change "P=0.Ol)" to --P=0.01)--.

Column 13, Line 29,(Approx.) Change "summarizes" to --summarized--.

Column 14, Line 36, Change "Nephropahty-" to --Nephropathy- --.

Column 14, Line 36, Change "Nephropahy+" to --Nephropathy+--.

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 1
ctggagacca ctcccatcct ttct                                          24

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 2
gatgtggcca tcacattcgt cagat                                         25

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 3
cagggtgctg tccacactgg acccc                                         25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 4
ccgtttgtgc agggcctggc tctct                                         25

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 5
aggcaatagg ttttgagggc cat                                           23

<210> SEQ ID NO 6
<211> LENGTH: 23
<212> TYPE: DNA
<213> ORGANISM: Artificial Sequence
<220> FEATURE:

-continued

```
<223> OTHER INFORMATION: Synthetic oligonucleotide primer

<400> SEQUENCE: 6
tcctccctgc tgctccgatt ccg                                           23

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 7
gaatcttaac atgctctgaa cc                                            22

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 8
gcccagccct atacctagt                                                19

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 9
cctttctgcc acgcggggcg cggg                                          24

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 10
catggctgct gcgctcccca g                                             21
```